US008593164B2

(12) United States Patent
Chandra et al.

(10) Patent No.: US 8,593,164 B2
(45) Date of Patent: Nov. 26, 2013

(54) CELL FOR BROADBAND DIELECTRIC SPECTROSCOPY

(75) Inventors: Satyan Chandra, Provo, UT (US); Brian Anthony Mazzeo, Provo, UT (US)

(73) Assignee: Brigham Young University (BYU), Provo, UT (US)

( * ) Notice: Subject to any disclaimer, the term of this patent is extended or adjusted under 35 U.S.C. 154(b) by 6 days.

(21) Appl. No.: 13/501,864

(22) PCT Filed: Oct. 15, 2010

(86) PCT No.: PCT/US2010/052914
§ 371 (c)(1),
(2), (4) Date: Apr. 13, 2012

(87) PCT Pub. No.: WO2011/047314
PCT Pub. Date: Apr. 21, 2011

(65) Prior Publication Data
US 2012/0200309 A1    Aug. 9, 2012

Related U.S. Application Data

(60) Provisional application No. 61/279,114, filed on Oct. 16, 2009.

(51) Int. Cl.
*G01R 27/08* (2006.01)

(52) U.S. Cl.
USPC ........ 324/693; 324/600; 324/718; 324/76.11; 324/76.38

(58) Field of Classification Search
USPC ............ 324/600–718, 76.11–76.38, 439–450
See application file for complete search history.

(56) References Cited

U.S. PATENT DOCUMENTS

| 5,288,613 | A | * | 2/1994 | Luong et al. | 435/25 |
| 5,976,338 | A | | 11/1999 | Fujita et al. | |
| 5,992,222 | A | * | 11/1999 | Belonenko et al. | 73/61.76 |
| 6,214,187 | B1 | * | 4/2001 | Hammond et al. | 204/450 |
| 6,566,079 | B2 | * | 5/2003 | Hefti | 506/9 |

(Continued)

FOREIGN PATENT DOCUMENTS

| EP | 1138758 A1 | 10/2001 |
| JP | 07244003 A * | 9/1995 |
| JP | 7244003 A1 | 9/1995 |

OTHER PUBLICATIONS

Mazzeo, Brian A., et al., "Observation of protein-protein interaction by dielectric relaxation spectroscopy of protein solutions for biosensor application", Applied Physics Letters, vol. 90, Issue 12, published on Mar. 21, 2007, pp. 123901-1-123901-3.

(Continued)

*Primary Examiner* — Jermele M Hollington
*Assistant Examiner* — Temilade S Rhodes-Vivour
(74) *Attorney, Agent, or Firm* — Brake Hughes Bellermann LLP

(57) ABSTRACT

In one general aspect, an apparatus can include a block defining a temperature control channel therethrough and a defining a sample chamber. The apparatus can also include an electrode disposed inside of the block such that the sample chamber is fluidically isolated from the temperature control channel by the electrode. The electrode can be configured to receive a signal from an impedance analyzer during a dielectric spectroscopy experiment related to a sample included in the sample chamber.

19 Claims, 10 Drawing Sheets

(56) References Cited

U.S. PATENT DOCUMENTS

| | | | |
|---|---|---|---|
| 7,514,938 B2* | 4/2009 | Publicover et al. | 324/663 |
| 7,594,983 B2 | 9/2009 | Sato | |
| 2004/0108857 A1* | 6/2004 | Jarski et al. | 324/464 |
| 2008/0248534 A1* | 10/2008 | Lim et al. | 435/91.2 |

OTHER PUBLICATIONS

Tirado, Monica C., et al., "Measurement of the Low-Frequency Dielectric Properties of Colloidal Suspensions: Comparison between Different Methods", Journal of Colloid and Interface Science, vol. 227, Jul. 2000, pp. 141-146.
"Liquid Parallel Plate Sample Cell", BDS1308, Retrieved on Jul. 3, 2007, web page available at: www.novocontrol.de/html/sa_cell_liquid.htm.
"Liquid Cylindrical Sample Cell", BDS1307, Retrieved on Jul. 5, 2007, web page available at: www.novocontrol.de/html/liquid_cell_guard.htm.
Mazzeo, Brian A., et al., "Two- and four-electrode, wide-bandwidth, dielectric spectrometer for conductive liquids: Theory, limitations, and experiment", Journal of Applied Physics, vol. 102, Issue 10, published on Nov. 19, 2007, pp. 104106-1-104106-6.
Hollingsworth, A. D., et al., "A broad frequency range dielectric spectrometer for colloidal suspensions: cell design, calibration, and validation", Journal of Colloid and Interface Science, vol. 257, May 1, 2003, pp. 65-76.
"Sample Cells Overview", Retrieved on May 17, 2005, web page available at: www.novocontrol.de/html/index_sample_cells.htm.
Feldman, Y. et al., "Time domain dielectric spectroscopy study of biological systems", IEEE Transactions on Dielectrics and Electrical Insulation, vol. 10, No. 5, Oct. 2003, pp. 728-753.
Kaatze, U. et al., "Broadband dielectric spectrometry of liquids and biosystems", Measurement Science and Technology, vol. 17, No. 2, Feb. 2006, pp. R17-R35.
Mazzeo, Brian A.,"Parasitic capacitance influence of potential-sensing electrodes on four-electrode liquid impedance measurements", Journal of Applied Physics vol. 105, No. 9, May 2009, pp. 094106-094106-5.
Ellison, W. J. et al., "Water: A dielectric reference", Journal of Molecular Liquids, vol. 68, No. 2, Apr. 1996, pp. 171-279.
Ellison, W. J.,"Permittivity of pure water, at standard atmosphereic pressure, over the frequency range 0-25 thz and the temperature range 0-100 degree c", Journal of Physical and Chemical Reference Data, vol. 36, Mar. 2007, pp. 1-18.
PCT/US2010/052914 International Search Report mailed Jun. 1, 2011, 8 pages.

* cited by examiner

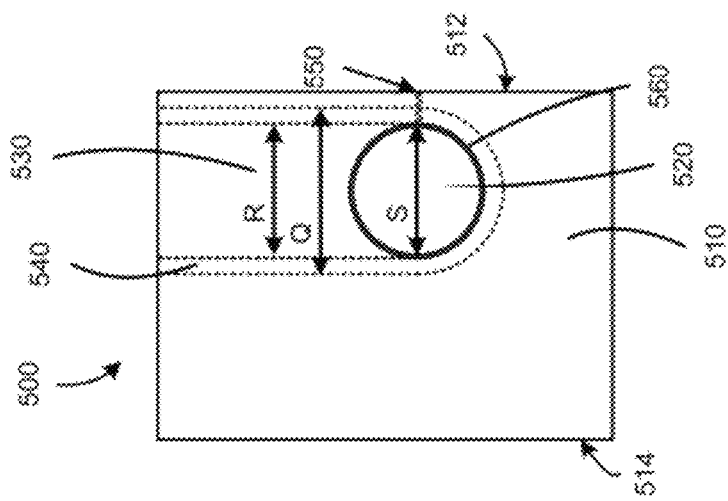
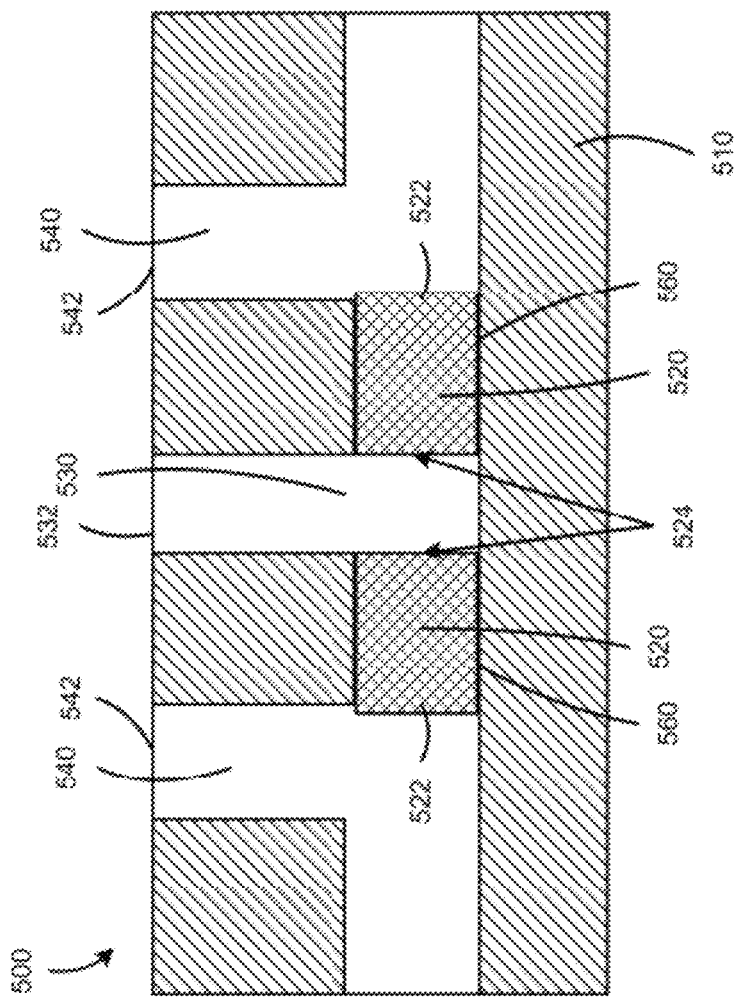
FIG. 5B
FIG. 5A

CELL FOR BROADBAND DIELECTRIC SPECTROSCOPY

RELATED APPLICATION

This application claims priority to and the benefit of PCT Application No. PCT/US10/52914, filed on Oct. 15, 2010, entitled, "CELL FOR BROADBAND DIELECTRIC SPECTROSCOPY", which claims priority to and the benefit of U.S. Provisional Patent Application Ser. No. 61/279,114, filed on Oct. 16, 2009, entitled, "TEMPERATURE-STABLE PARALLEL PLATE DIELECTRIC CELL FOR BROADBAND LIQUID IMPEDANCE MEASUREMENTS," both of which are incorporated herein by reference in their entireties.

TECHNICAL FIELD

This description relates to a dielectric cell for broadband dielectric spectroscopy experiments.

BACKGROUND

Liquid electrical measurements of sample solutions, which can be performed using dielectric spectroscopy (also can be referred to as dielectric impedance spectroscopy or as impedance spectroscopy) techniques, can be used to determine a broad variety of phenomena from physical and/or chemical processes occurring within sample solutions. Dielectric spectroscopy has historically been used, for example, for protein measurements to compute the dipole moment under varying sample solution conditions. Developments in equipment such as dielectric cells over the past century have greatly enhanced the ability of researchers to access important dielectric properties using dielectric spectroscopy experiments, however, known dielectric cells for broadband dielectric spectroscopy experiments are unable to provide measurements of samples in solution in a desirable fashion due to unfavorable conductivity of the sample solution, unwanted electrode polarization, relatively poor temperature control, electromagnetic frequency limitations, and/or lack of titration capability. Thus, a need exists for systems, methods, and apparatus to address the shortfalls of present technology, and to provide other new and innovative features.

SUMMARY

In one general aspect, an apparatus can include a block defining a temperature control channel therethrough and a defining a sample chamber. The apparatus can also include an electrode disposed inside of the block such that the sample chamber is fluidically isolated from the temperature control channel by the electrode. The electrode can be configured to receive a signal from an impedance analyzer during a dielectric spectroscopy experiment related to a sample included in the sample chamber.

In another general aspect, an apparatus can include a block defining a temperature control channel therethrough and defining a first portion of a sample chamber 1. The apparatus can also include an electrode disposed inside of the block such that a first surface of the electrode is exposed within the sample chamber and a second surface of the electrode is exposed within the temperature control channel. The first portion of the sample chamber can be fluidically isolated from the temperature control channel by the electrode.

In yet another general aspect, a method can include forming at least a portion of an electrode channel within a block and forming a sample chamber within the block such that the sample chamber is in fluid communication with the portion of the electrode channel. The method can also include disposing an electrode inside of the electrode channel of the block such that a surface of the electrode defines at least a portion of the sample chamber.

The details of one or more implementations are set forth in the accompanying drawings and the description below. Other features will be apparent from the description and drawings, and from the claims.

BRIEF DESCRIPTION OF THE DRAWINGS

FIG. 5A is a cross-sectional diagram of a dielectric cell, according to an embodiment.

FIG. 5B is a diagram that illustrates a side view of the dielectric cell shown in FIG. 5A.

DETAILED DESCRIPTION

Figure 1:
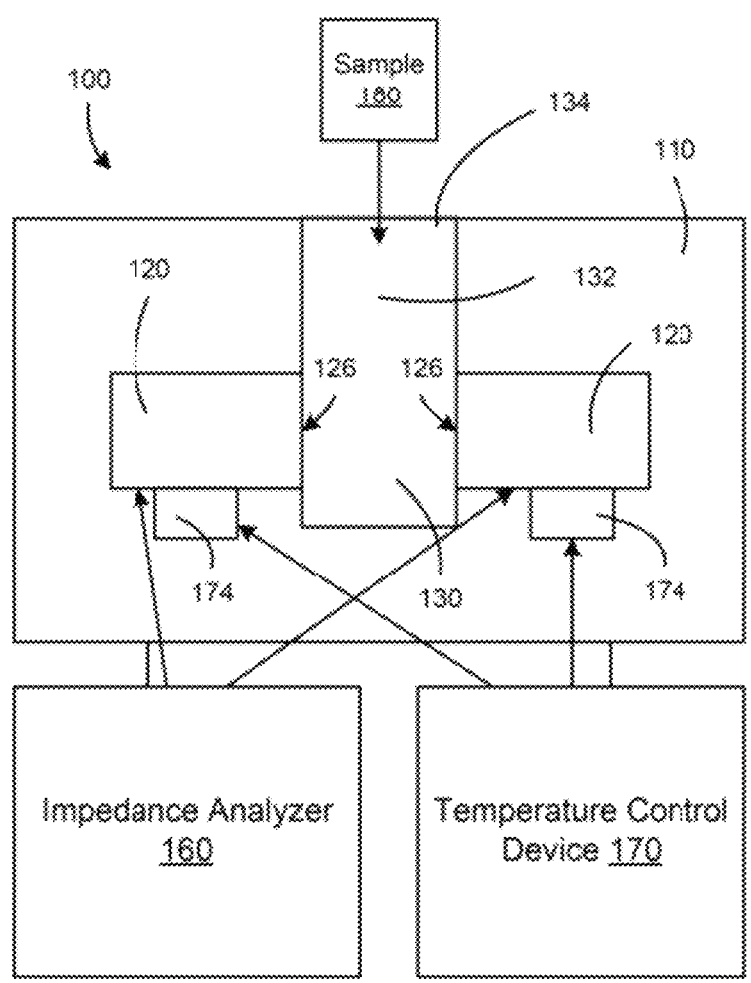
FIG. 1 is a block diagram that illustrates a dielectric cell configured for use in a broadband dielectric spectroscopy experiment.

FIG. 1 is a block diagram that illustrates a dielectric cell 100 configured for use in a broadband dielectric spectroscopy (also can be referred to as impedance spectroscopy) experiment. During a dielectric spectroscopy experiment using the dielectric cell 100, an electromagnetic field can be applied at various frequencies (e.g., a range of frequencies) to a sample 180 (e.g., a liquid sample, a sample solution) so that one or more dielectric properties of the sample 180 (e.g., electric dipole moment of the sample expressed as permittivity) can be measured as a function of frequency. Using such measurements, a relatively broad variety of phenomena of the sample 180, such as physical and/or chemical processes occurring within the sample, can be derived. Dielectric spectroscopy can be used to measure the properties of various types of samples such as organic compounds (e.g., cells, proteins, polymers), inorganic compounds (e.g., salts, metals, minerals), and/or so forth.

As shown in FIG. 1, the dielectric cell 100 is coupled to an impedance analyzer 160 and a temperature control device 170. The dielectric cell 100 has electrodes 120 disposed within (e.g., embedded within) a block 110 of the dielectric cell 100 and a sample chamber 130 in which the sample 180 can be disposed (e.g., injected) via an opening 134 during the dielectric spectroscopy experiment. The sample 180 can be any type of sample that can be the subject of a dielectric spectroscopy experiment. The sample 180 can be disposed in the sample chamber 130 so that, during a dielectric spectroscopy experiment, an electromagnetic field can be applied to the sample 180 by the impedance analyzer 160 via the electrodes 120 and dielectric properties of the sample can be measured by the impedance analyzer 160 via the electrodes 120.

As shown in FIG. 1, the sample chamber 130 is defined, at least in part, by the block 110. In other words, an inner surface of the sample chamber 130 is defined by the block 110. In some embodiments, the sample chamber 130 can be defined by boring a hole into the block 110, which can be monolithically formed.

As shown in FIG. 1, the electrodes 120 each have a surface 126 that is exposed within the sample chamber 130. In some embodiments, the surface 126 can be referred to as chamber surfaces or as active surfaces of the electrodes 120. Accordingly, the sample 180, when disposed within the sample chamber 130, can come in contact with each of the surfaces 126 of the electrodes 120. In some embodiments, the surface 126 of each of the electrodes 120 can be referred to as defining at least a portion of the surface of the sample chamber 130. As shown in FIG. 1, the surface 126 of the electrode 120 on the right side of the block 110 faces the surface 126 of the electrode on the left side of the block 110 so that the surfaces 126 are parallel (or substantially parallel). In other words, the surface 126 of the electrode 120 on the right side of the block 110 is disposed within a plane that is parallel to a plane including the surface 126 of the electrode 120 on the left side of the block 110.

In some embodiments, one or more of the electrodes 120 can be made of an electrically conductive material and/or a material that is resistant to (e.g., substantially resistant to) corrosion by materials (e.g., fluids) used during a dielectric spectroscopy experiment. For example, one or more of the electrodes 120 can be made of an elemental material such as copper, gold, platinum, and so forth. In some embodiments, for example, one or more of the electrodes 120 can be made of an alloy material such as stainless steel (e.g., 304 stainless steel, 305 stainless steel, 316L stainless steel).

In some embodiments, one or more of the electrodes 120 can have various shapes. For example, one or more of the electrodes 120 can have a cylindrical shape, a square shape, a rectangular shape, and/or so forth. Thus, the surface 126 of each of the electrodes 120 can be a circle, an oval, a square, a rectangle, and/or so forth.

The temperature control device 170 is configured to control (e.g., maintain) a temperature of the sample chamber 130 (and the sample 180 included therein) and/or the electrodes 120 using temperature elements 174 during an dielectric spectroscopy experiment. In some embodiments, the temperature elements 174 can be, for example, an electric heating element and/or cooling element that can be used to heat and/or cool the electrodes 120 during a dielectric spectroscopy experiment. In some embodiments, one or more of the temperature elements 174 can be a temperature control channel through which a temperature control fluid can flow during a dielectric spectroscopy experiment. In some embodiments, a temperature of the sample 180, when in the sample chamber 130, can be maintained at a desirable set point temperature via heating and/or cooling of the electrodes 120 (by the temperature elements 174).

As shown in FIG. 1, one or more of the temperature elements 174 can be in contact with one or more of the electrodes 120. In some embodiments, one or more of the temperature elements 174 may not be in contact with one or more of the electrodes 120.

The block 110 can be made of any type of electrically insulating and/or temperature insulating material. In some embodiments, the block 110 can also be made of a material that is resistant to (e.g., substantially resistant to) corrosion that could be caused by certain types of chemicals used in dielectric spectroscopy experiments. In some embodiments, the block 110 can be made of a polymeric material. In some embodiments, the block 110 can be made of, for example, polytetrafluoroethylene (PTFE) (i.e., Teflon) (which can have a relatively low thermal conductivity of approximately 0.26 Watts/Kelvin-meter). In some embodiments, the block 110 can be a monolithic block (formed monolithically from a material) into which the electrodes 120 and/or the temperature elements 174 are embedded. More details related to formation of the block 110 and the dielectric cell 100 are described below.

In some embodiments, the impedance analyzer 160 can be any type of impedance analyzer (e.g., an Agilent 4294A impedance analyzer, a 6500B Wayner Kerr Impedance Analyzer) that can be used during a dielectric spectroscopy experiment. In some embodiments, the impedance analyzer 160 can be configured to induce an electromagnetic field over a wide range of frequencies from a few microhertz ($\mu$Hz) (e.g., 1 $\mu$Hz) to gigahertz (GHz) (e.g., 0.1 GHz, 1 GHz, 10 GHz). In some embodiments, one or more probes from the impedance analyzer 160 can be inserted into one or more holes (e.g., probe channels) formed within (e.g., drilled into) the block 110 and contacted with one or more of the electrodes 120. In some embodiments, the dielectric cell 100 can be used, in conjunction with the impedance analyzer 160, to measure, for example, dielectric relaxations due to overall protein dipole moments over a broadband range of frequencies from a few hertz (Hz) to hundreds of megahertz (MHz) (e.g., 40 Hz to 110 MHz) in a desirable fashion. In some embodiments, the primary, or beta, relaxation of, for example, a protein molecule can occur in the MHz range due to the hydrodynamic properties of the molecule in a sample solution. In this frequency range, the major obstacles to accurate measurements of proteins in solution can be, for example, conductivity of the solution, electrode polarization, temperature variation, insufficient handling of broadband frequencies, and/or lack of titration capability.

Although not shown in FIG. 1, in some embodiments, the impedance analyzer 160 and/or the temperature control device 170 can be controlled by a computing device. Also, data from the impedance analyzer 160 and/or the temperature control device 170 can be analyzed at the computing device. For example, the impedance analyzer 160 and/or the temperature control device 170 can be controlled via software such as LabVIEW executing on a computing device. In some embodiments, the computing device can be, for example, a wired device and/or a wireless device (e.g., wi-fi enabled device) and can be, for example, a computing entity (e.g., a personal computing device), a mobile phone, a personal digital assistant (PDA), a server device (e.g., a web server), a host device, and/or so forth. The computing device can be configured to operate based on one or more platforms (e.g., one or more similar or different platforms) that can include one or more types of hardware, software, firmware, operating systems, runtime libraries, and/or so forth. In some embodiments, the computing device can be a cluster of devices (e.g., a server farm).

In some embodiments, the impedance analyzer 160 and/or temperature control device 170 can be configured to operate within a network. In other words, the impedance analyzer 160 and/or temperature control device 170 can be configured to function within various types of network environments that can include one or more client devices and/or one or more server devices. For example, the network can be, or can include, a local area network (LAN), a wide area network (WAN), and/or so forth. The network can be, or can include, a wireless network and/or wireless network implemented using, for example, gateway devices, bridges, switches, and/or so forth. The network can include one or more segments and/or can have portions based on various protocols such as Internet Protocol (IP) and/or a proprietary protocol. The network can include at least a portion of the Internet.

Various features related to dielectric cells, such as dielectric cell 100 shown in FIG. 1, are described in connection with the remaining figures. Although each of the dielectric cells typically includes more than one electrode (e.g., a pair of electrodes such as the pair of electrodes 120 shown in FIG. 1), the dielectric cells will generally be discussed in terms of features related to a single electrode because the features related to the single electrode may, in some embodiments, be mirrored within each side of the dielectric cells. In some embodiments, features related to a electrode on one side of a dielectric cell may not be mirrored on another side of the dielectric cell.

Figure 2A:
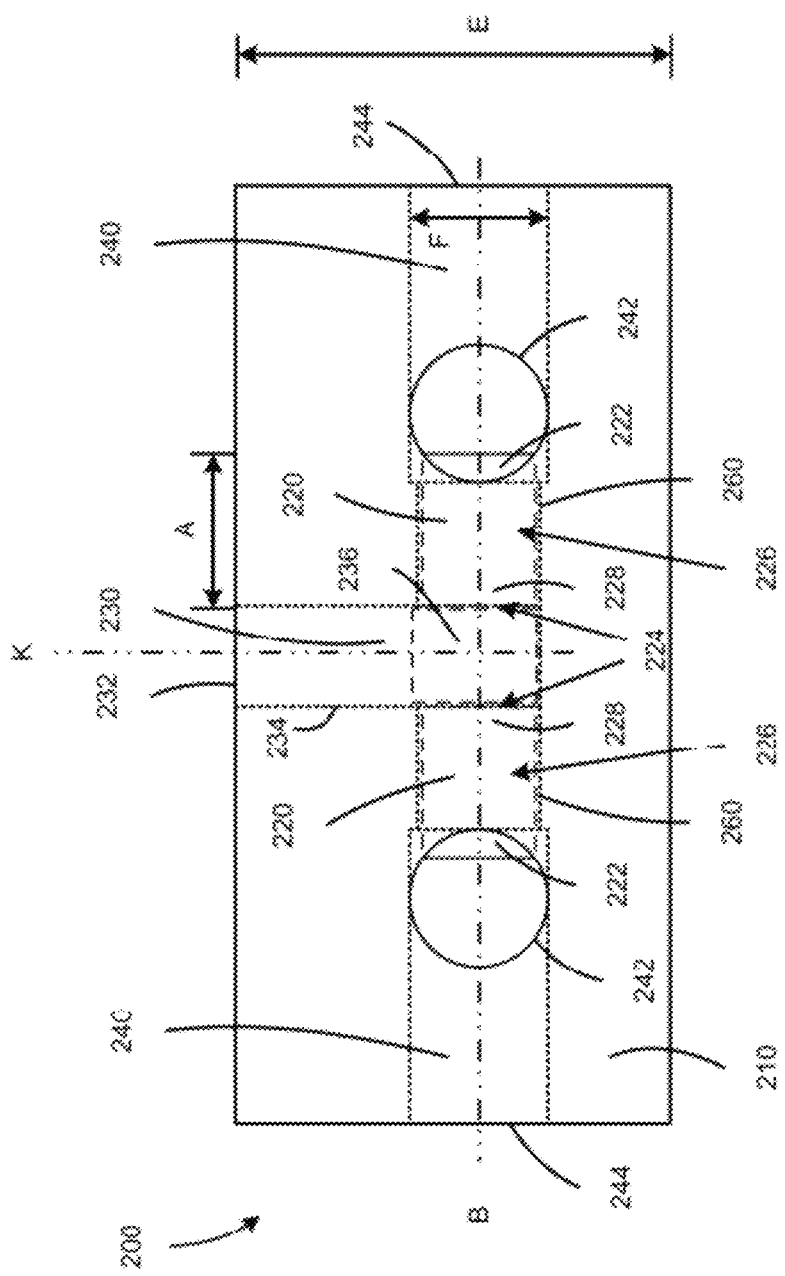
FIG. 2A is a diagram that illustrates a front view of a dielectric cell.
Figure 2C:
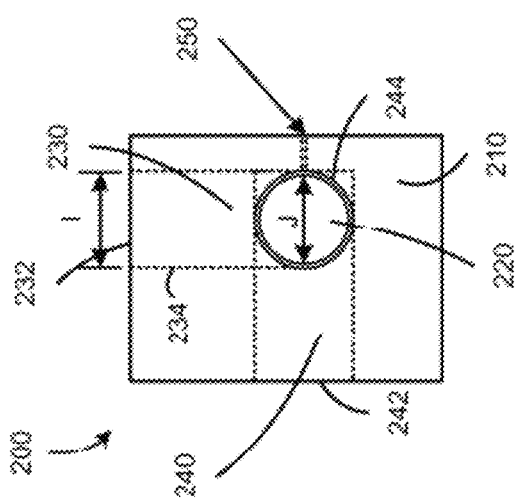
FIG. 2C is a diagram that illustrates a side view of the dielectric cell shown in FIGS. 2A and 2B.
Figure 2B:
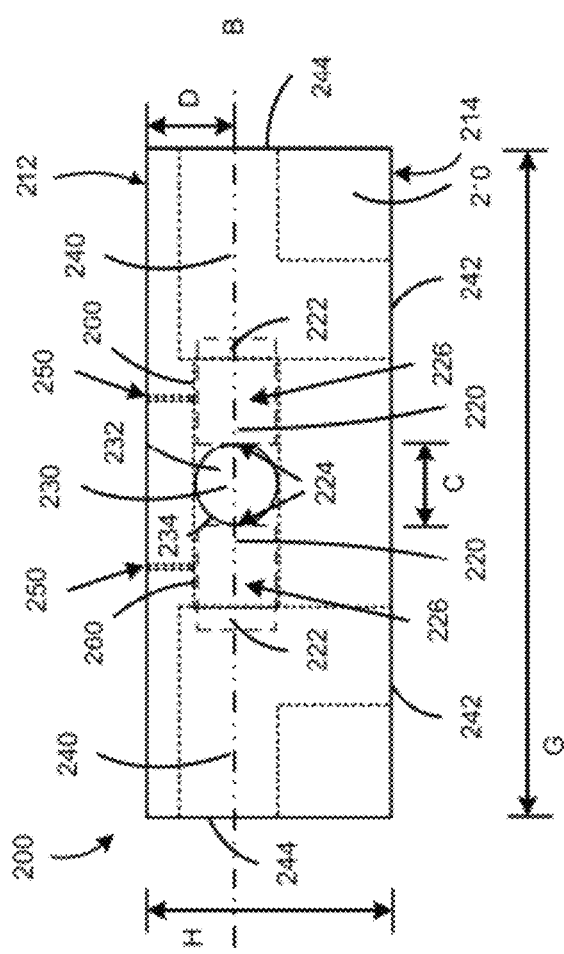
FIG. 2B is a diagram that illustrates a top view of the dielectric cell shown in FIG. 2A.

FIGS. 2A through 2C are diagrams that illustrate an example of a dielectric cell 200, according to an embodiment. Specifically, FIG. 2A is a diagram that illustrates a front view of a dielectric cell 200, and FIG. 2B is a diagram that illustrates a top view of the dielectric cell shown in FIG. 2A. FIG. 2C is a diagram that illustrates a side view of the dielectric cell shown in FIGS. 2A and 2B.

As shown in FIG. 2A, the dielectric cell 200 is defined by a block 210 that defines a sample chamber 230. An electrode 220 (shown, at least in part, with dashed lines) is embedded within the block 210, and a surface 224 on a distal end 228 of the electrode 220 defines at least a portion of the sample chamber 230. In this embodiment, the surface 224 of the electrode 220 is aligned along a surface 234 of sample chamber 230 that defines at least a portion of the sample chamber 230. In some embodiments, the surface 234 of the sample chamber 230 can define a first portion of the sample chamber 230 and the surface 224 of the electrode 220 can define a second portion of the sample chamber 230. In some embodiments, the sample chamber 230 may not be vertically oriented as shown in FIG. 2A.

In some embodiments, the surface 224 of the electrode 220 can be polished. In some embodiments, the surface 224 of the electrode 220 can be polished so that electrical parasitic effects (e.g., electrode polarization, parasitic surface charges) related to the surface 224 of the electrode 220 can be reduced in a desirable fashion. In some embodiments, on the low-frequency side (i.e., the MHz range and below) of a dielectric spectroscopy experiment, electrode polarization can be a dominant parasitic influence. Electrode polarization can be caused by the formation of a layer of charge on and/or near the surface of the surface 224 of the electrode 220. Because electrode polarization can be in series with the measurement of the sample solution (e.g., protein) properties included in the sample chamber 230, electrode polarization can disrupt accurate measurements of the permittivity of, for example, the sample solution. In some embodiments, the surface 224 the electrode 220 can be mechanically polished. In some embodiments, the surface 224 the electrode 220 can be polished with, for example, 600, 800, and 1200 grit silicon carbide abrasive discs in a Spectrum System 2000 (LECO Corp.).

As shown in FIG. 2A, a temperature control channel 240 is defined by the block 210. The temperature control channel 240 is between an opening 242 on the front side of the block 210 and an opening 244 on a side (a right side and a left side) of the block 210. The temperature control channel 240 is configured so that a temperature control fluid (e.g., deionized (DI) water, oil, liquid nitrogen, antifreeze) can flow through the temperature control channel 240 from outside of the block 210 via the opening 242 and/or the opening 244. For example, a temperature control fluid can be pumped into the opening 244 through the temperature control channel 240 and out of the opening 242. In some embodiments, the temperature control channel 240 can have a diameter F of between a few millimeters (e.g., 2 mm, 11 mm) and a several centimeters (e.g., 3 cm). In some embodiments, the block 210 can have a height E of between several millimeters (e.g., 3 mm, 8 cm) and a several centimeters (e.g., 3.5 cm, 5 cm, 10 cm). In some embodiments, the temperature control channel 240 can have a diameter F that is approximately one-third (or less) of the height E of the block 210.

As shown in FIG. 2A, the electrode 220 has a proximal end 222 (opposite the surface 224 on the distal end 228 of the electrode 220) that is at least partially disposed within the temperature control channel 240. The proximal end 222 of the electrode 220 can project into the temperature control channel 240. Although not shown in FIG. 2A, in some embodiments, the proximal end 222 of the electrode 220 may not project into the temperature control channel 240.

Because at least a portion of the proximal end 222 of the electrode 220 is disposed within the temperature control channel 240, a temperature control fluid that flows through the temperature control channel 240 can come in contact with the proximal end 222 of the electrode 220. Thus, the temperature of the electrode 220 can be controlled by a temperature control fluid flowing through the temperature control channel 240. In some embodiments, a temperature of the electrode 220 during a dielectric spectroscopy experiment can be between −50° C. and 200° C. In some embodiments, a temperature control fluid through the temperature control channel 240 can see deionized (DI) water pumped from a NESLAB RTE-40 thermal bath that has a temperature between 5° C. to 55° C.

Because the dielectric cell 200 has a temperature control channel 240, immersing the dielectric cell 200 in a bath to control temperature (of the sample chamber 230) may not be required. This is contrasted with many known cells that require complete immersion into a bath. Immersion into a bath, however, can prevent the introduction of reaction agents into the known cells without disturbing the finely tuned characteristics of the known cells. Temperature control can be critical in a dielectric spectroscopy experiment. For example, in precision protein experiments, the dielectric increment associated with proteins is an order of magnitude smaller than the background permittivity of the solution. In some cases, stability of the medium is critical so the small permittivity signal can be extracted. The permittivity of water can be noticeably dependent on temperature, and the relaxation characteristics of proteins may also be dependent on temperature.

In some embodiments, a length A of the electrode can be defined so that a temperature gradient between the proximal end 222 of the electrode 220 and the surface 224 of the electrode 220 may be relatively small. In some embodiments, the length A of the electrode 220 can be between approximately a millimeter (mm) (e.g., 1 mm, 10 mm) and several centimeters (cm) (e.g., 2 cm, 5 cm). In some embodiments, a temperature gradient from the proximal end 222 and the surface 224 of the electrode 220 can be determined so that a temperature of the surface 224 of the electrode 220 can be calculated (and controlled) based on a temperature of a temperature control fluid flowing through the temperature control channel 240. Because the temperature of the electrode 220 (and the sample chamber 230) can be controlled by a temperature control fluid via the temperature control channel 240, immersion of the dielectric cell 200 into a temperature bath to control temperature of the sample chamber 230 may be avoided.

As shown in FIG. 2A, the electrode 220 is disposed within an electrode channel 260 between the sample chamber 230 and the temperature control channel 240. The electrode 220 can be disposed within the electrode channel 260 so that the temperature control channel 240 is fluidically isolated from the sample chamber 230 by the electrode 220 (e.g., a medial portion 226 of the electrode 220). In other words, the electrode 220 can be disposed within the electrode channel 260 so that a fluid from the temperature control channel 240 may not leak into the sample chamber 230, and vice versa. If the electrode 220 were not disposed within the electrode channel 260, the temperature control channel 240 would be in fluid communication with the sample chamber 230.

As shown in FIG. 2A, the electrode 220 is aligned along an axis B that is orthogonal to (or substantially orthogonal to) an axis K along which the sample chamber 230 is aligned. Specifically, the electrode 220 is aligned along the axis B so that the surface 224, which is exposed within the sample chamber 230, is orthogonal to the axis B. As shown in FIG. 2A, both of the electrodes 220 are aligned along the axis B. Although not shown in FIG. 2A, in some embodiments, the electrode 220 may be aligned along an axis that is not orthogonal to an axis along which the sample chamber 230 is aligned. In such embodiments, the sample chamber 230 can be aligned along an axis that is non-parallel with an axis along which the electrode 220 is aligned.

In some embodiments, the electrode 220 can be disposed within the electrode channel 260 so that the temperature control channel 240 is fluidically isolated from the sample chamber 230. In some embodiments, the electrode 220 can be fixedly disposed within the electrode channel 260 so that the temperature control channel 240 is fluidically isolated from the sample chamber 230. In some embodiments, for example, the electrode 220 (or at least a medial portion 226 of the electrode 220) can be press fit into the electrode channel 260. In such embodiments, the electrode channel 260 can be defined by the block 210 such that the electrode 220 is press fit into the electrode channel 260. In some embodiments, at least a portion of the electrode channel 260 and/or at least a portion of the electrode 220 can be chamfered (e.g., tapered) so that the electrode 220 may be moved into the electrode 260 a desirable fashion. In some embodiments, the electrode channel 260 can be tapered (tapered from the temperature control channel 240 towards the sample chamber 230) so that as the electrode 220 is advanced in the electrode channel 260, the electrode 220 may be tightly press fit into the electrode channel 260. More details related to moving an electrode into an electrode channel are described in connection with, for example, FIG. 3D.

Although not shown in FIG. 2A, in some embodiments, the electrode 220 can be fixedly disposed within the electrode channel 260 using, for example, glue (e.g., epoxy), a set screw, a gasket around the electrode 220, and/or so forth. In some embodiments, the electrode 220 can be threaded so that the electrode 220 can be screwed into the electrode channel 260. In such embodiments, the electrode channel 260 can also be threaded such that the electrode channel 260 can receive the threaded electrode 220.

In some embodiments, the electrode 220 can be disposed within the block 210 so that a known surface area (of the surface 224) of the electrode 220 is exposed within the sample chamber 230. Thus, the surface area of the electrode 220 that may come in contact with a sample within the sample chamber 230 can also be known. In some embodiments, the electrode 220 may be disposed within the block 210 so that only the surface 224 of the electrode 220 (not a side wall of the electrode 220) is exposed within the sample chamber 230.

Although not shown in FIG. 2A, after a sample has been disposed within the sample chamber 230 during a dielectric spectroscopy experiment a cover can be placed over and/or within an opening 232 of the sample chamber 230. The cover can be placed over and/or within the opening 232 so that the sample included in the sample chamber 230 may not be disturbed in an undesirable fashion (e.g., exposed to ambient conditions, exposed to potential contaminants) during the dielectric spectroscopy experiment. In some embodiments, a Teflon cap, a rubber bung, and/or so forth can be used as a cover.

As shown in FIG. 2A, the sample chamber 230 can include a sample region 236 into which a sample may be disposed during a dielectric spectroscopy experiment. As shown in FIG. 2A, when a sample is disposed within the sample region 236, an air gap may exist between the sample and a cover over and/or within the opening 232. The air gap may allow for expansion and/or contraction of the sample during a dielectric spectroscopy experiment (e.g., during thermal cycling of the dielectric spectroscopy experiment) without overfilling the sample chamber 230. In some embodiments, the air gap may allow for the addition of (e.g., introduction of) a material (e.g., a portion of a sample) into the sample chamber 230 during a dielectric spectroscopy experiment (e.g., during titration during a dielectric spectroscopy experiment). In some embodiments, the sample region 236 can have a volume of approximately 10 to 5,000 microliters ($\mu L$).

In some embodiments, a cover over and/or within the opening 232 can be temporarily removed during a dielectric spectroscopy experiment so that one or more materials (including a portion of a sample) can be added to and/or removed from the sample chamber 230. For example, a material can be added to a sample already disposed within the sample chamber 230 during a dielectric spectroscopy experiment. In some embodiments, the material may be added to the sample to titrate the sample. Thus, the material can be added to a sample already disposed within the sample chamber so that the material may react with the sample.

As another example, a first portion of a sample may be added to the sample chamber 230 during a first portion of a dielectric spectroscopy experiment. A cover may be placed within the opening 232 of the sample chamber during the first portion of the dielectric spectroscopy experiment. During a second portion of the dielectric spectroscopy experiment, the cover may be temporarily removed so that a second portion of the sample may be added to the sample chamber 230 via the opening 232 of the sample chamber 230. During a third portion of the dielectric spectroscopy experiment, the cover may be temporarily removed so that a portion of the sample may be removed from the sample chamber 230 via the opening 232 of the sample chamber 230.

In some embodiments, titration (e.g., titration of hen lysozyme (HENL) and beta-lactoglobulin (BLG)) may be performed during a dielectric spectroscopy experiment so that a baseline may be established for electrode polarization and/or solvent permittivity (associated with a sample). In some embodiments, removing and/or adding one or more materials (e.g., liquids) can be considered perturbations that can be measured relative to the baseline. In some embodiments, an assumption can be made that electrode polarization may be relatively constant during a dielectric spectroscopy experiment. In some embodiments, this method (which can be referred to as a differential method) can be used to resolve relatively low concentrations of, for example, proteins by suppressing background parasitic contributions (such as electrode polarization). In some embodiments, computer control may be used to record repeated measurements and/or to plot time-resolved studies of protein interactions.

Although not shown, in some embodiments, the dielectric cell 200 can include a mechanism configured to mix a sample included in the sample chamber 230. For example, a magnetic stir bar can be included in the sample chamber 230. The magnetic stir bar may be used to agitate a sample included in the sample chamber 230 via an apparatus outside of the sample chamber 230 that is configured to cause the magnetic stir bar to move (e.g., to rotate).

FIG. 2B is a diagram that illustrates a top view of the dielectric cell shown in FIG. 2A. As shown in FIG. 2B, the temperature control channel 240 has an L shape. In some embodiments, the temperature control channel 240 can have a different shape than the L shape shown in FIG. 2B. For example, the temperature control channel 240 can be a relatively straight channel that is diagonally disposed between opening 242 and opening 244. In some embodiments, the temperature control channel 240 can have one or more curved portions. An example of a temperature control channel having a different shape than that shown in FIG. 2B is shown in connection with FIGS. 6A and 6B.

As shown in FIG. 2B, the surface 234 of the sample chamber 230 of the block 210 defines a cylindrical shape. In some embodiments, the sample chamber 230 can have a different shape than that shown in FIG. 2B. For example, the sample chamber 230 can be shaped like a box or can have one or more curved portions. Thus, the opening 232 of the sample chamber 230 can have, for example, a square or rectangular shape.

As shown in FIG. 2B, the electrodes 220 are disposed within the block 210 so that the surface 224 of each of the electrodes 220 directly face one another. Specifically, the electrodes 220 are disposed within the block 210 so that the electrodes 220 are aligned along a common axis B. Thus, in some embodiments, the surface 224 of the electrode right side of the block 210, when projected along axis B onto the surface 224 of the electrode 220 on the left side of the block 210, will be precisely disposed over the surface 224 electrode 220 on the left side of block 210.

As shown in FIG. 2B, the surfaces 224 of the electrodes 220 may be parallel (or substantially parallel) to one another. Specifically, the surface 224 of the electrode 220 on the left side of the block 210 may be disposed within (aligned along) a plane that is parallel to a plane including the surface 224 of the electrode 220 on the right side of the block 210.

In some embodiments, a distance C between the surfaces 224 of the electrodes 220 can be defined (e.g., defined to be relatively large) so that electrical noise (e.g., a parasitic capacitance, electrode polarization in series with a sample in the sample chamber 230) associated with the electrodes 220 may be reduced (e.g., minimized) in a desirable fashion. For example, the distance C between the surfaces 224 of the electrodes 220 can be defined so that a parasitic capacitance between the electrodes 220 may be negligible and may not affect a dielectric spectroscopy experiment in an undesirable fashion.

In some embodiments, the distance C may be defined (e.g., defined to be relatively small) so that a temperature gradient within the sample chamber 230 may be reduced (e.g., minimize) in a desirable fashion. Specifically, the distance C may be defined so that a temperature gradient from the surfaces 224 of the electrodes 220 to, for example, the approximate middle of the sample region 236 may be relatively small. Having a relatively small temperature gradient within the sample chamber 230 may be desirable because the temperature of the sample chamber 230 may be maintained using a temperature control fluid flowing through the temperature control channels 240 via the electrodes 220.

In some embodiments, the distance C can be between a few millimeters (e.g., 1 mm) to several centimeters (e.g., 2 cm, 5 cm, 10 cm). In some embodiments, the distance C can be defined based on balancing of parasitic capacitance between the electrodes 220 and temperature gradient within the sample chamber 230. In other words, the distance C can be defined to optimize for a relatively low parasitic capacitance and a relatively low temperature gradient within the sample chamber 230. In some embodiments, the distance C can be between 0.5 to 1.5 times the length A of the electrode 220.

As shown in FIG. 2B, the block 210 defines a probe channel 250 between the electrode channel 260 and the ambient environment outside of the block 210. Thus, the electrode 220 can be accessed via the probe channel 250. The probe channel 250 can be defined by the block 210 so that one or more probes can be connected to the electrode 220 from, for example, an impedance analyzer to the electrode 220. In some embodiments, the one or more probes can be coupled to (e.g., glued within, a press fit within) the probe channel 250 and/or coupled to (e.g., soldered to) the electrode 220. For example, the probe channel 250 can be configured so that an electrically conductive screw (which can be connected to a probe) can be inserted into (e.g., screwed into) the probe channel 250 and contacted with the electrode 220. In some embodiments, the probe channel 250 can be a tapped hole (e.g., a tapped hole configured to receive a screw with a 2-56 size).

As shown in FIG. 2B, the axis B, along which the electrodes 220 are aligned, is closer to a back side 212 of block 210 than a front side 214 of the block 210. Accordingly, the electrodes 220 are disposed within the block 210 so that they are closer to the back side 212 of the block 210 than the front side 214 of the block 210. Because the electrodes 220 may be closer to the back side 212 of the block 210, electrical signals from an impedance analyzer (not shown) coupled to the electrodes 220 may travel a shorter distance (and be subject to less electrical noise) than if the electrodes 220 were centered within the block 210 (from the perspective of the top view of the block 210).

In some embodiments, the electrodes 220 may be aligned along the axis B and not aligned closer to the back side 212 of the block 210 (than that shown in FIG. 2B) so that the electrodes 220 may not be susceptible to ambient conditions (e.g., ambient temperature conditions) in contact with the back side 212 of the block 210. In other words, the electrodes 220 may be offset from the back side 212 of the block 210 so that the electrodes 220 may be insulated by (e.g., adequately insulated by) the block 210 and a temperature of the electrodes 220 may be controlled in a desirable fashion using the temperature control channels 240. In some embodiments, a distance D can be approximately a third of a distance H (which is the width of the block 210). In some embodiments, the distance H can be a few centimeters (e.g., 0.5 cm, 4 cm, 10 cm). In some embodiments, a length G of the block 210 can be several centimeters (e.g., 20 cm, 75 cm, 100 cm). In some embodiments, the length A of the electrodes 220 can be 3 to 10 times shorter than the length G of the block 210.

As shown in FIG. 2B, at least a portion of the temperature control channel 240 is aligned along the axis B, which is the axis along which the electrode 220 is aligned. Although not shown in FIG. 2B, in some embodiments, the portion of the temperature control channel 240 may not be aligned along the axis B. An example of a dielectric cell that has a temperature control channel that is not aligned along an axis along which the electrode 220 is aligned is described in connection with FIGS. 6A and 6B.

In some embodiments, additional probe channels (in addition to probe channel 250) can be defined within the block 210. In some embodiments, a probe channel can be defined within the block 210 in a different location than the probe channel 250 shown in FIG. 2B. For example, a probe channel can be defined within the block 210 between the electrode 220 and a front side 214 of the block 210 rather than between the electrode 220 and the back side 212 of the block 210. In some embodiments, a probe channel can be defined within a bottom portion and/or a top portion of the block 210.

FIG. 2C is a diagram that illustrates a side view of the dielectric cell shown in FIGS. 2A and 2B. As shown in FIG. 2C, electrode 220 has a cylindrical shape. In some embodiments, the electrode 220 can have a different shape than that shown in FIG. 2C. For example, the electrode 220 can have various polygon shapes such as a rectangular shape and/or so forth. In some embodiments, diameter J of the electrode 220 can be between a few millimeters (e.g., 2 mm, 5 mm) and several centimeters (e.g., 1 cm, 3 cm). As described above, the electrode 220 can be made of various types of electrically conductive materials such as stainless steel.

In some embodiments, a cross-sectional area of the sample chamber 230 can be equal to (or substantially equal to) a cross-sectional area of the electrode 220. As shown in FIG. 2C, a diameter I (which is approximately the same as distance C) of the sample chamber 230 is equal to (or substantially equal to) a diameter J of the electrode 220. Although not shown, in some embodiments, a diameter I of the sample chamber 230 can be greater than or smaller than the diameter J of the electrode 220.

As shown in FIGS. 2A through 2C, the volume of the electrode 220 is relatively small compared with the volume of the block 210. In some embodiments, the volume of the electrode 220 can be approximately equal to the volume of the sample chamber 230 and/or the sample region 236. In other words, the volume of the electrode 220 can be on the same order of magnitude as the volume of the sample chamber 230. In some embodiments, the volume of the electrode 220 can be greater than or less than the volume of the sample chamber 230. In some embodiments, the relatively small size of each of the electrodes 220 can result in a relatively small parasitic capacitance between the electrodes 220.

Although not shown in FIGS. 2A through 2C, in some embodiments, one or more portions of the dielectric cell 200 can be formed using, for example, an injection molding process. In some embodiments, the block 210 of the dielectric cell 200 can be formed from a monolithic piece of a material such as Teflon. Thus, the block 210 of the dielectric cell 200 can be referred to as being monolithically formed.

In some embodiments, the dielectric cell 200 can be made of a material (e.g., Teflon) that can be cleaned in a desirable fashion. For example, the dielectric cell 200 can be made of a material that can be autoclaved and/or cleaned with solvents to remove, for example, organic contaminants.

Although not shown in FIGS. 2A through 2C, the sample chamber 230 can have multiple portions. In other words, the sample chamber 230 can be divided into separate sections into which different samples may be inserted so that the different samples within the separate sections of the sample chamber 230 may not be mixed. Also, although not shown in FIGS. 2A through 2C, one or more of the channels (e.g., the temperature control channel 240) can include one or more valves to control fluid flow into the channels. In some embodiments, a fluid flow control mechanism, such as a valve, can be included in the sample chamber 230.

FIGS. 3A through 3E are diagrams that collectively illustrate a method for producing a dielectric cell 300. FIG. 3F is a diagram that illustrates the dielectric cell 300 shown in FIGS. 3A through 3E coupled to an impedance analyzer 395.

Figure 3A:
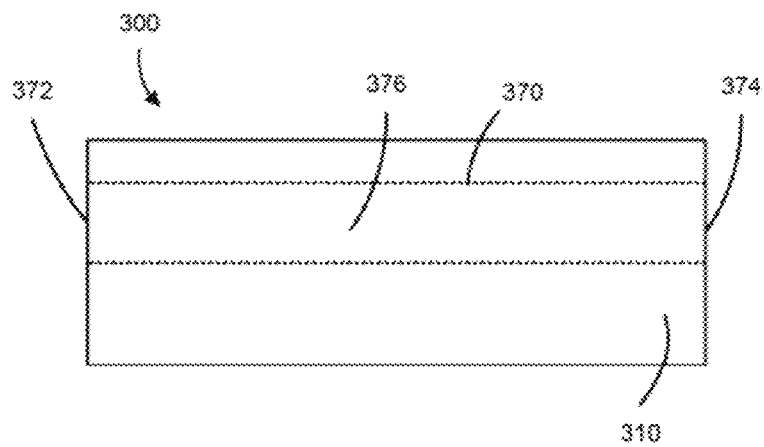
FIG. 3A is a diagram that illustrates at least a portion of an electrode channel defined in a dielectric cell.

FIG. 3A is a diagram that illustrates at least a portion of a channel 370 defined in a dielectric cell 300. In some embodiments, the portion of the channel 370 can be formed (e.g., defined) using, for example, a tool such as a drill and a drill bit. As shown in FIG. 3A, the channel 370 has an opening 372 on one end (e.g., on one side) of the channel 370 and an opening 374 on another end (e.g., on another side) of the channel 370 within a block 310 of the dielectric cell 300. A medial portion 376 of the channel 370 defines at least a portion of an electrode channel 360 shown in FIG. 3B. In some embodiments, the block 310 can be made of a material such as Teflon. In some embodiments, the block 310 can have a different shape than that shown in FIG. 3A. For example, the block 310 can have one or more curved sides, more sides than shown in FIG. 3A, and/or so forth.

Figure 3B:
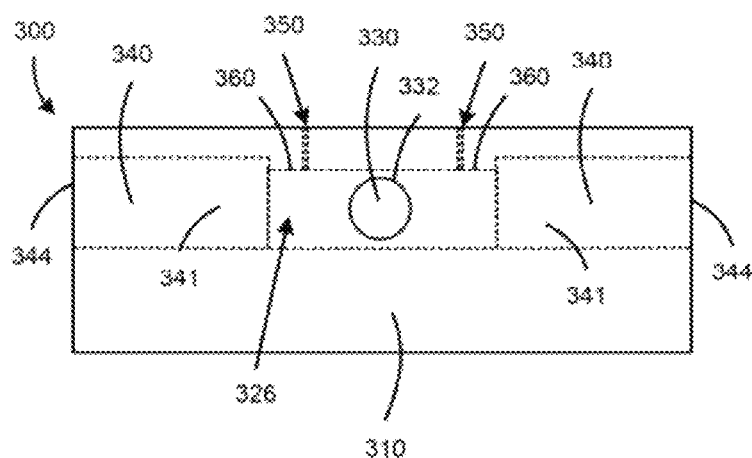
FIG. 3B is a diagram that illustrates a sample chamber and at least a portion of a temperature control channel in the dielectric cell shown in FIG. 3A.

FIG. 3B is a diagram that illustrates a sample chamber 330 and at least a portion 341 of a temperature control channel 340 in the dielectric cell 300 shown in FIG. 3A. In some embodiments, the portion 341 of the temperature control channel 340 can be formed within the block 310 by boring at least a portion of the channel 370 to a larger diameter as shown in FIG. 3B for form openings 344. As shown in FIG. 3B, the portion of the channel 370 remaining is an electrode channel 360. As shown in FIG. 3B, the sample chamber 330 is defined within the block 310 so that an opening 332 is on a side of the block 310 that is different than an opening 344 of the temperature control channel 340.

In this embodiment, a probe channel 350 is defined within the block 310 so that an ambient environment outside of the block 310 is in fluid communication with the electrode channel 360. The probe channel 350 can be a conduit through which a probe can be contacted with an electrode (not shown) when the electrode is inserted into the electrode channel 360. At this point, the portion 341 of the temperature control channel is in fluid communication with the sample chamber 330 via the electrode channel 360 as shown in FIG. 3B.

Figure 3C:
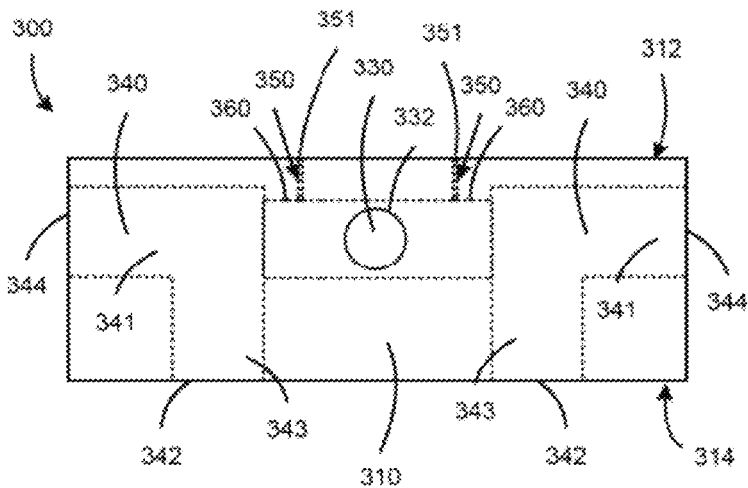
FIG. 3C is a diagram that illustrates another portion of the temperature control channel in the dielectric cell shown in FIG. 3B.

FIG. 3C is a diagram that illustrates another portion 343 of the temperature control channel 340 in the dielectric cell 300 shown in FIG. 3B. As shown in FIG. 3C, an opening 342 of the temperature control channel 340 is on a side (i.e., a back side 312) of the block 310 that is different than a side of the block 310 on which the opening 344 of the temperature control channel 340 is disposed.

As shown in FIG. 3C, the probe channel 350 has an opening 351 on the backside 312 of the block 310, and the temperature control channel 340 has an opening 342 on a front side 314 of the block 310. Thus, the opening 351 of the probe channel 350 is on a side that is opposite a side including the opening 342 of the temperature control channel 340.

Figure 3D:
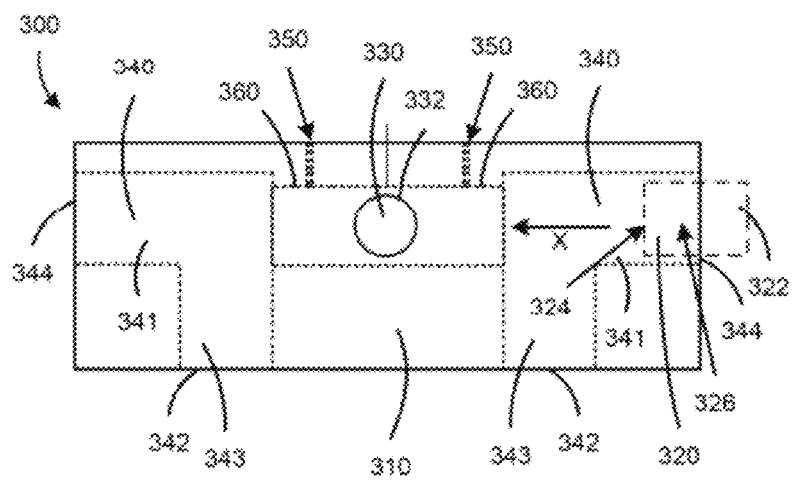
FIG. 3D is a diagram that illustrates insertion of an electrode into the electrode channel shown in FIG. 3C.
Figure 3E:
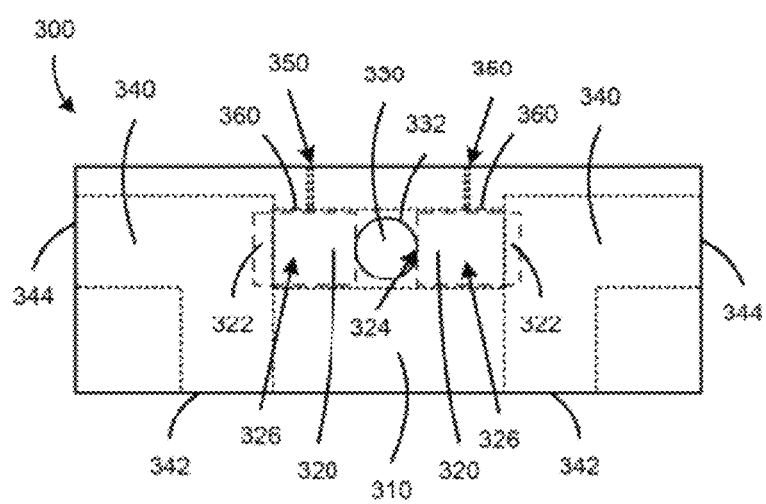
FIG. 3E is a diagram that illustrates the dielectric cell after electrodes have been inserted into the dielectric cell shown in FIG. 3D.
Figure 3F:
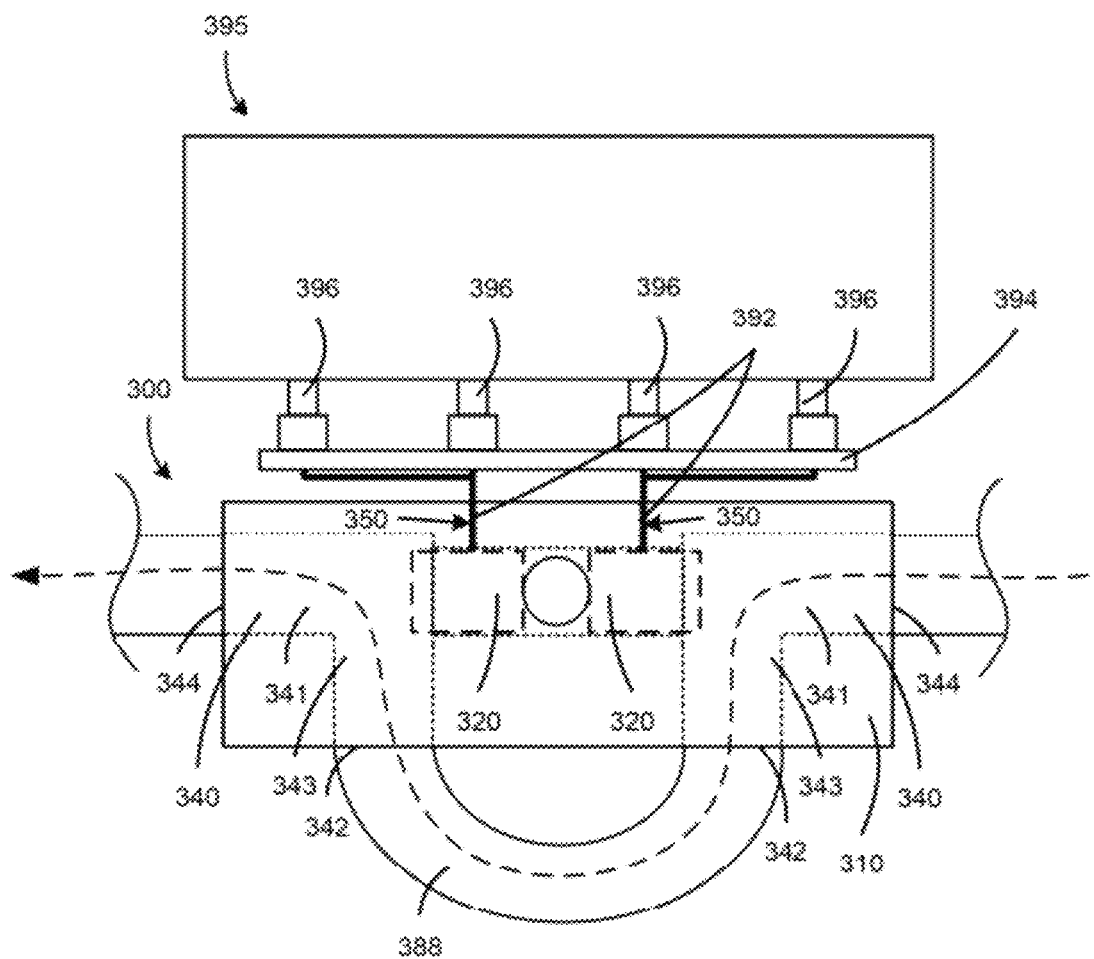
FIG. 3F is a diagram that illustrates the dielectric cell coupled to an impedance analyzer, according to an embodiment shown in FIG. 3E.

FIG. 3D is a diagram that illustrates insertion of an electrode 320 into the electrode channel 360 shown in FIG. 3C. As shown in FIG. 3D, a surface 324 of the electrode 320 (on a distal end of the electrode 320) is moved along direction X through the portion 341 of the temperature control channel 340 (on the right side of the dielectric cell 300) until the surface 324 of the electrode is at sample chamber 330 as shown in FIG. 3E. Although not shown in FIG. 3D, in a similar fashion, a second electrode can be inserted into the portion 341 of the temperature control channel 340 on the left side of the dielectric cell 300 (in a direction opposite direction X) until the second electrode has a surface that is at the sample chamber 330. In some embodiments, the electrode 320 can be, for example, press fit and/or glued into the electrode channel 360.

In some embodiments, the temperature control channel 340 may not have a diameter that is larger than a diameter of the electrode channel 360. In such embodiments, the portion 341 of the temperature control channel 340 may have a diameter that is the same as a diameter of the electrode channel 360. In such embodiments, the portion 341 of the temperature control channel 340 may be formed as shown in FIG. 3A, without being bored to a larger diameter as shown in FIG. 3B.

FIG. 3E is a diagram that illustrates the dielectric cell 300 after electrodes 320 have been inserted into the dielectric cell 300 shown in FIG. 3D. As shown in FIG. 3E, when the electrodes 320 are disposed within the block 310 of the dielectric cell 300, the temperature control channels 340 are no longer in fluid communication with the sample chamber 330. Specifically, the sample chamber 330 is fluidically isolated from the temperature control channels 340 by at least medial portions 326 of the electrodes 320.

FIG. 3F is a diagram that illustrates the dielectric cell 300 coupled to an impedance analyzer 395, according to an embodiment. As shown in FIG. 3F, the impedance analyzer 395 is a four-probe impedance analyzer 395 that is coupled to the electrodes 320 using probes 392 via the probe channels 350. Each of the two probes 392 can be electrically connected to the four connectors 396 through, for example, a conductive connector (e.g., wires, metal connections) to a shorting bar or wire between high potential and high current terminals of the impedance analyzer 395 and to a shorting bar or wire between the low potential and low current terminals of the impedance analyzer 395. In some embodiments, the probes 392 can be operably coupled to (e.g., mechanically connected to) the impedance analyzer 395 via a plate 394 (e.g., a plastic plate that provides insulation, a metal plate (which may or may not be electrically connected to a ground or a virtual ground or guard)). In some embodiments, the plate 394 can be replaced with a different shaped object such as a box that is disposed around the dielectric cell 300. Also, as shown in FIG. 3F, a temperature control fluid can flow (as represented by the arrow) from the temperature control channel 340 on the right side of the dielectric cell 300 to the temperature control channel 340 on the left side of the dielectric cell 300 via a tube 388.

Although not shown in FIG. 3F, in some embodiments, an electrical guarding element (e.g., a metal plate) can be coupled to the dielectric cell 300 (e.g., a bottom portion of the dielectric cell 300, surrounding the dielectric cell 300) when the impedance analyzer 395 is coupled to the dielectric cell 300 during a dielectric spectroscopy experiment. In some embodiments, the plate 394 can function as the electrical guarding element. In some embodiments, the electrical guarding element can be configured to provide Gaussian shielding. In some embodiments, the impedance analyzer 395 can have a virtual ground output (not shown) that can be coupled to the electrical guarding element coupled to the dielectric cell 310. In some embodiments, the virtual ground can be configured, for example, to balance power (e.g., current) through the impedance analyzer 395 and/or to shield stray fields (e.g., electromagnetic fields) that could influence measurements (in an adverse fashion) of the impedance analyzer 395 and/or the dielectric cell 310 during a dielectric spectroscopy experiment.

Figure 4:
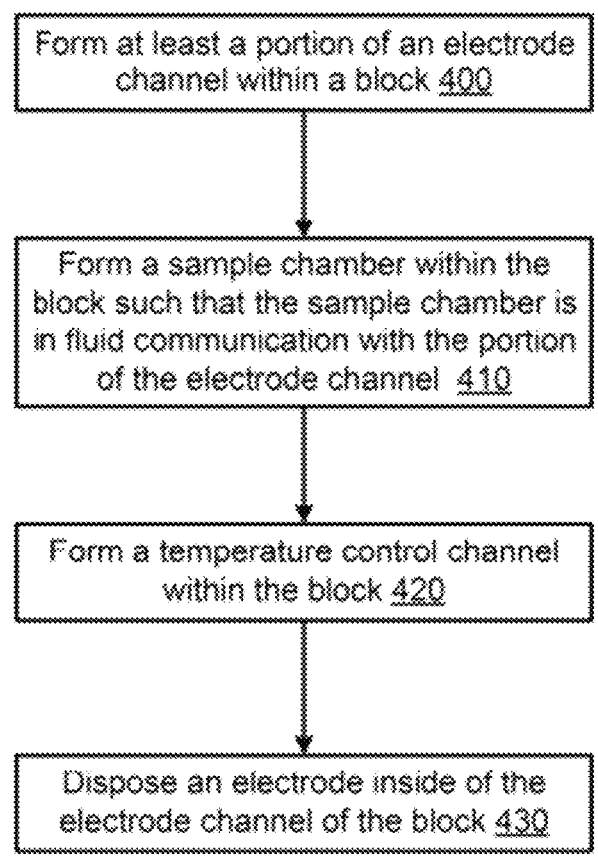
FIG. 4 is a flowchart that illustrates a method for producing a dielectric cell.

FIG. 4 is a flowchart that illustrates a method for producing a dielectric cell. As shown in FIG. 4, at least a portion of an electrode channel is formed within a block (block 400). In some embodiments, the electrode channel can have a shape configured to receive electrode to be inserted into the electrode channel. In some embodiments, the electrode channel can have a diameter that is approximately equal to a diameter of an electrode to be inserted into the electrode channel.

A sample chamber is formed within the block such that the sample chamber is in fluid communication with the electrode channel (block 410). In some embodiments, the sample chamber can be aligned along a first axis that is non-parallel to a second axis along which electrode channel is aligned. In some embodiments, the sample chamber can be aligned along a first axis that is orthogonal to (or substantially orthogonal to) a second axis along which electrode channel is aligned. In some embodiments, a diameter (or cross-sectional area) of the sample chamber can be approximately equal to a diameter (or cross-sectional area) of the electrode channel.

The temperature control channel is formed within the block (block 420). In some embodiments, the temperature control channel can have at least a portion that is aligned along a first axis that is parallel to (substantially parallel to) a second axis along which the electrode channel is aligned. In some embodiments, at least a portion of the electrode channel can be bored to a larger diameter to define a portion of the temperature control channel. In other words, the portion of the temperature control channel can be defined from the portion of the electrode channel.

An electrode can be disposed inside of the electrode channel of the block (block 430). In some embodiments, the electrode can be press fit into the electrode channel of the block. In some embodiments, the electrode can be, for example, a stainless steel electrode.

FIG. 5A is a cross-sectional diagram of a dielectric cell 500, according to an embodiment. The dielectric cell 500 includes an electrode 520 embedded within a block 510. The electrode 520 has a surface 524 that is exposed within a sample chamber 530 defined by the block 510. The block 510 also defines a temperature control channel 540. The electrode 520 has a proximal end 522 that is exposed within the temperature control channel 540. As shown in FIG. 5A, the sample chamber 530 has an opening 532 that is on a same side as an opening 542 of the temperature control channel 540. Also, as shown in FIG. 5A, the temperature control channel 540 has an L shape. In this embodiment, the electrode 520 can be inserted into an electrode channel 560 via the temperature control channel 540.

FIG. 5B is a diagram that illustrates a side view of the dielectric cell 500 shown in FIG. 5A. As shown in FIG. 5B, the sample chamber 530 has a diameter R that is approximately equal to a diameter S of the electrode 520. The temperature control channel 540 has a diameter Q that is greater than the diameter R of the sample chamber 530. Also as shown in FIG. 5B, the block 510 defines a probe channel 550 which a probe (not shown) associated with an impedance analyzer (not shown) can be coupled to the electrode 520 during a dielectric spectroscopy experiment. As shown in FIG. 5B, the electrode 520 is disposed within the block 510 so that a distance between the electrode 520 and a backside 512 of the block 510 is shorter than a distance between the electrode 520 and a front side 514 of the block 510.

Figure 6B:
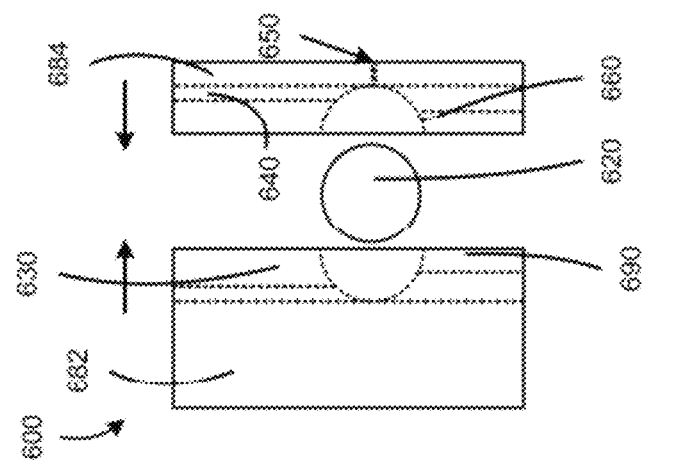
FIG. 6B is a diagram that illustrates a side view of the dielectric cell shown in FIG. 6A before the electrode is enclosed within separate portions of the dielectric cell.
Figure 6A:
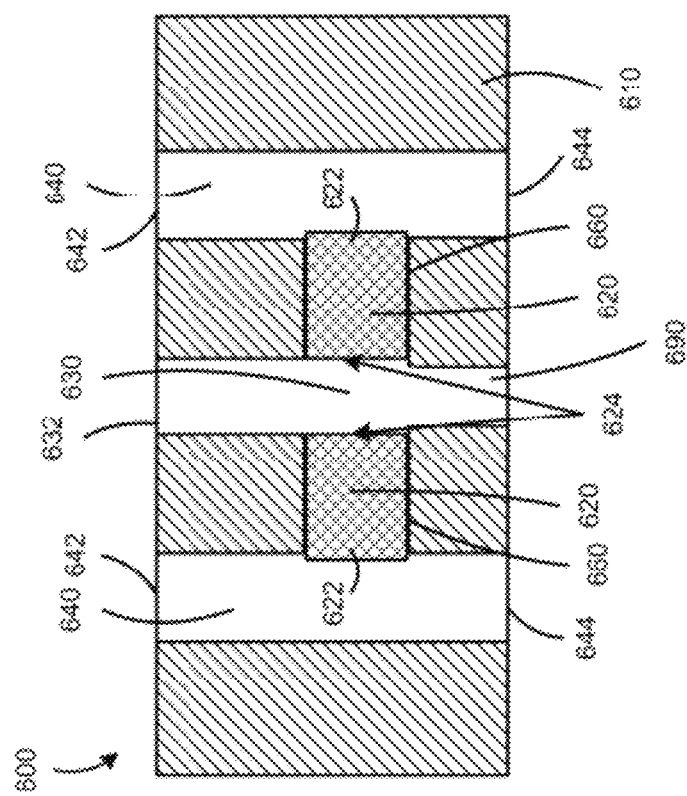
FIG. 6A is another cross-sectional diagram of a dielectric cell, according to an embodiment.

FIG. 6A is another cross-sectional diagram of a dielectric cell 600, according to an embodiment. The dielectric cell 600 includes an electrode 620 embedded within a block 610. The electrode 620 has a surface 624 that is exposed within a sample chamber 630 defined by the block 610. The block 610 also defines a temperature control channel 640. The electrode 620 has a proximal end 622 that is exposed within the temperature control channel 640. As shown in FIG. 6A, the sample chamber 630 has an opening 632 that is on a same side as an opening 642 of the temperature control channel 640. The temperature control channel 640 also has an opening 644 that is opposite the opening 642 of the temperature control channel 640. Thus as shown in FIG. 6A, the temperature control channel 640 is aligned approximately along a line and is vertically oriented within the dielectric cell 600 (when the dielectric cell 600 is oriented as shown in FIG. 6A).

Also, as shown in FIG. 6A, the dielectric cell 600 includes a drain channel 690. The drain channel 690 can be used to drain one or more portions of a sample from the sample chamber 630 during any portion of a dielectric spectroscopy experiment. For example, a sample can be drained from the sample chamber 630 via the drain channel 690 upon the completion of a dielectric spectroscopy experiment. In some embodiments, the dielectric cell 600 can be oriented as shown in FIG. 6A during a dielectric spectroscopy experiment. Accordingly, the sample can be drained from the sample chamber 630 by gravitational forces.

In this embodiment, the electrode 620 may not be inserted into an electrode channel 660 via the temperature control channel 640. In this embodiment, the electrode 620 is embedded within the block 610 when the electrode 620 is enclosed within two separate portions that define the block 610. The two separate portions that define the block 610 are shown in FIG. 6B.

FIG. 6B is a diagram that illustrates a side view of the dielectric cell 600 shown in FIG. 6A before the electrode 620 is enclosed within separate portions of the dielectric cell 600. As shown in FIG. 6B, the block 610 of the dielectric cell 600 is formed as (or cut into) two separate portions—portion 682 (shown on the left side of figure) and portion 684 (shown on the right side of figure). As illustrated by the arrow shown in FIG. 6B, the electrode 620 can be enclosed within the portions 682, 684 when the two separate portions 682, 684 of the dielectric cell are moved around the electrode 620 (and coupled together using, for example, a screw, glue, and/or so forth).

In some embodiments, the separate portions 682, 684 can be cut into the separate portions 682, 684 from a monolithic block 610 formed using, for example, the techniques shown in connection with FIGS. 3A through 3F. In some embodiments, the separate portions 682, 684 can be each be formed (e.g., formed separately) from separate block materials. As shown in FIG. 6B, the portion 682 and portion 684 are different sizes. In some embodiments, the portion 682 and the portion 684 can be defined so that they are the same size (or approximately the same size).

As shown in FIG. 6B, a first portion of the temperature control channel 640 is included in portion 682, and a second portion of the temperature control channel 640 is included in portion 684. Similarly, a first portion of the sample chamber 630 and a first portion of the drain 690 are included in portion 682, and a second portion of the sample chamber 630 and a second portion of the drain 690 are included in portion 684. Also as shown in FIG. 6B, the block 610 defines a probe channel 650 which a probe (not shown) associated with an impedance analyzer (not shown) can be coupled to the electrode 620 during a dielectric spectroscopy experiment.

Figure 7:
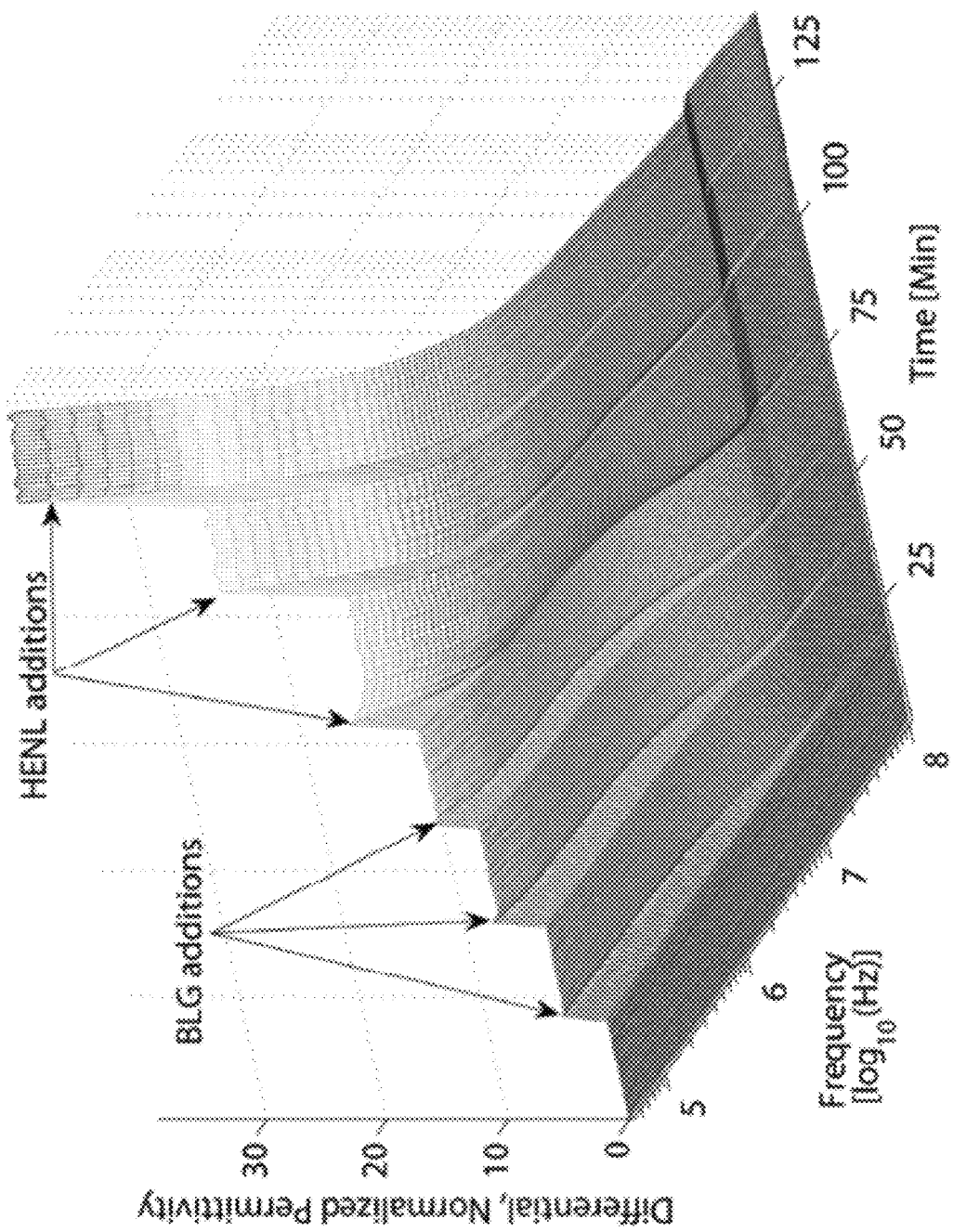
FIG. 7 is a graph that illustrates experimental data related to a dielectric cell, according to an embodiment.

FIG. 7 is a graph that illustrates experimental data related to a dielectric cell, according to an embodiment. In some embodiments, the dielectric cell can be a dielectric cell such as dielectric cell 100 shown in FIG. 1. The graph illustrates temperature control of the dielectric cell, the ability of the dielectric cell to resolve protein relaxations at least up to 110 MHz, and the successful measurement of temperature-dependent sample solution permittivity and protein titrations.

To establish a baseline dielectric cell constant, the following approach was used. A water bath for use as a temperature control fluid was set to 25° C. and was allowed to stabilize for 15 minutes. The capacitance the dielectric cell at 1 MHz was measured with the dielectric cell empty and then with 800 μl of DI water added to the dielectric cell followed by 15 minutes of stabilization time. Using these values of capacitance, C, the cell constant, α, and the parasitic capacitance, $C_P$, were determined using values of 1 and 78.368 for the DI water through the formula $$C = \alpha \in + C_P. \tag{2}$$

The measured cell constant was calculated to be 0.0494 picofarads (pF) and the parasitic capacitance was calculated at 0.712 pF at 1 MHz.

To test the ability of the dielectric cell to scale through a range of temperatures, the temperature was scaled from 5° C. to 55° C. in 5° increments. The water bath was held at the set temperature for approximately 15 minutes before multiple frequency sweeps were performed. The permittivity of the water at 1 MHz was measured and verified as being in agreement with standards, in particular, within the 15° to 40° range (which can cover many physiological temperatures).

Next, a titration of beta-lactoglobulin (BLG) and hen lysozyme (HENL) was performed in the dielectric cell. Beta-lactoglobulin (L3908) and hen lysozyme (L6876) were obtained from Sigma and reconstituted in 0.1 millimolar (mM) hydrochloric acid (HCl) at a concentration of 20 mg/ml. The solutions were mixed and stored in microcentrifuge tubes. The cell was rinsed with ethanol and DI water and allowed to dry. The 0.1 mM HCl solution was placed in the dielectric cell and baseline measurements were taken at 25° C.

The sweeps (referenced above) were post-processed in MATLAB and analyzed. A shift in the capacitance due to the impedance analyzer range shift was removed. Additionally, the data was normalized to 110 MHz. Differential measurements were then taken with respect to the original 0.1 mM HCl baseline to remove effects of electrode polarization. Least-squares fittings were done with the function "lsqcurve-fit", with frequencies expressed logarithmically. Measurements of permittivity were fitted to the real part of a single relaxation Cole-Cole curve $$\varepsilon = \varepsilon_\infty + \frac{\Delta\varepsilon}{1 + j(\tau\omega)^{(1-\alpha)}} \tag{3}$$

where $\in_\infty$ is the high frequency permittivity, $\Delta\in$ is the change in permittivity, α is the Cole parameter describing the spread of the relaxation [26], τ is the relaxation time, and $j=\sqrt{-1}$. The electric dipole moment is related to $\Delta\in$ through the Oncley formula $$\mu = \sqrt{\frac{2Mk_bT\varepsilon_0\delta}{Ng}} \quad (4)$$

where μ is the dipole moment, M is the protein molecular weight in kilodaltons, $k_b$ is the Boltzmann constant, T is the temperature in Kelvin, $\in_0$ is permittivity of free space, N is Avogadro's number, g is the correlation parameter assumed to be 1 for dilute protein solutions, and $\delta = \lim_{c \to 0} \Delta\in/c$ is the dielectric increment where c is the protein concentration in mg/ml. Assuming the protein is roughly spherical, the effective hydrodynamic radius of the protein can be estimated by the formula $$\tau = \frac{4\pi\eta a^3}{k_bT} \quad (5)$$

where a is the effective hydrodynamic radius and η is the viscosity of the solvent.

Using Equation 5, the hydrodynamic radii of BLG and HENL were estimated to be 26 Å and 20 Å respectively, these values being similar to structural data deposited in the Protein Data Bank. Estimated dipole moments of BLG and HENL were 800±40 debye (D) and 270±20 D. The value for BLG is in good agreement with the value measured by the pioneering work of Ferry and Oncley of 720 D. In some embodiments, measurements on lysozyme can have a dipole moments of around 400 D in water, around 300 D in water from pH 4 to pH 6, and 210 D in water in other experiments, indicating the results were within the expected range.

Continuous dielectric measurements were then taken of a protein titration. A pipettor was used to remove 60 μl of liquid from the sample chamber of the dielectric cell. Sixty μl of the concentrated BLG solution was then added to the sample chamber of the dielectric cell to form a concentration of 1.5 mg/ml. After each titration, the sample solution was allowed to stabilize for 20 minutes to reach thermal and chemical equilibrium. Sixty μl of liquid was again removed and 60 μl of the concentrated BLG solution was added to form ~3 mg/ml BLG solution. Then 60 μl of the solution was removed and 60 μl of concentrated HENL solution was added. This step of removing 60 μl of solution and adding 60 μl of concentrated HENL was repeated twice.

The results of this titration are shown in the graph in FIG. 7. The graph illustrate that the interaction between these two proteins (BLG and HENL). When just one protein is present, the dielectric relaxation for that protein is visible. When the complementary protein is added, the dielectric relaxation shifts to lower frequencies. This shift takes place because the aggregate is now much bigger than the individual proteins that constitute the aggregate. The increased hydrodynamic volume may impede the rotation of the aggregate. Also, the data may indicate that electrode polarization is affecting the measurements as the concentration of dissolved ions in the solution increases. However, this dielectric cell has relatively low polarization below 1 MHz as compared with other known experimental apparatus.

These dielectric spectroscopy experiments illustrate that the dielectric cell (and variations) described herein can stabilize temperature for dielectric spectroscopy experiments and can resolve protein titrations in solution in a desirable fashion. The dielectric cell described herein can be used to perform accurate and repeatable measurements of protein solutions for comparison with theoretical determination of protein electrical parameters.

Implementations of the various techniques described herein may be implemented in digital electronic circuitry, or in computer hardware, firmware, software, or in combinations of them. Implementations may implemented as a computer program product, i.e., a computer program tangibly embodied in an information carrier, e.g., in a machine-readable storage device (computer-readable medium) or in a propagated signal, for processing by, or to control the operation of, data processing apparatus, e.g., a programmable processor, a computer, or multiple computers. A computer program, such as the computer program(s) described above, can be written in any form of programming language, including compiled or interpreted languages, and can be deployed in any form, including as a stand-alone program or as a module, component, subroutine, or other unit suitable for use in a computing environment. A computer program can be deployed to be processed on one computer or on multiple computers at one site or distributed across multiple sites and interconnected by a communication network.

Method steps may be performed by one or more programmable processors executing a computer program to perform functions by operating on input data and generating output. Method steps also may be performed by, and an apparatus may be implemented as, special purpose logic circuitry, e.g., an FPGA (field programmable gate array) or an ASIC (application-specific integrated circuit).

Processors suitable for the processing of a computer program include, by way of example, both general and special purpose microprocessors, and any one or more processors of any kind of digital computer. Generally, a processor will receive instructions and data from a read-only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in special purpose logic circuitry.

To provide for interaction with a user, implementations may be implemented on a computer having a display device, e.g., a cathode ray tube (CRT) or liquid crystal display (LCD) monitor, for displaying information to the user and a keyboard and a pointing device, e.g., a mouse or a trackball, by which the user ca provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Implementations may be implemented in a computing system that includes a back-end component, e.g., as a data server, or that includes a middleware component, e.g., an application server, or that includes a front-end component, e.g., a client computer having a graphical user interface or a Web browser through which a user can interact with an implementation, or any combination of such back-end, middleware, or front-end components. Components may be interconnected by any form or medium of digital data communication, e.g., a communication network. Examples of communication networks include a local area network (LAN) and a wide area network (WAN), e.g., the Internet.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments. It should be understood that they have been presented by way of example only, not limitation, and various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

What is claimed is:

1. An apparatus, comprising:
   a block defining a temperature control channel therethrough and a defining a sample chamber, the block being made of an electrically insulating material; and
   an electrode disposed inside of the block such that the sample chamber is fluidically isolated from the temperature control channel by the electrode, the electrode configured to receive a signal from an impedance analyzer during a dielectric spectroscopy experiment related to a sample included in the sample chamber, the electrode being made of an electrically conductive material, the block defining a probe channel configured to receive a probe of the impedance analyzer, the probe channel being disposed between the electrode and a back side of the block, the electrode being aligned along an axis such that a surface of the electrode that is exposed within the sample chamber is orthogonal to the axis, a distance between the axis and the back side of the block being shorter than a distance between the axis and a front side of the block.

2. The apparatus of claim 1, wherein the sample chamber is configured to receive a sample through an opening of the sample chamber, the temperature control channel is configured to receive a temperature control fluid during the dielectric spectroscopy experiment.

3. The apparatus of claim 1, wherein the block is a monolithic block.

4. The apparatus of claim 1, wherein the block defines a probe channel in fluid communication with a portion of the electrode disposed between the temperature control channel and the sample chamber, the probe channel being fluidically isolated from the temperature control channel and the sample chamber.

5. The apparatus of claim 1, wherein the electrode has a diameter smaller than a diameter of the temperature control channel, the diameter of the electrode is substantially equal to a diameter of an opening of the sample chamber.

6. The apparatus of claim 1, wherein the electrode has a volume that is the same order of magnitude as a volume of the sample chamber.

7. The apparatus of claim 1, wherein the electrode is aligned along a first axis non-parallel to a second axis along which the sample chamber is aligned.

8. An apparatus, comprising:
   a block defining a temperature control channel therethrough and defining a portion of a sample chamber, the block being made of an electrically insulating material; and
   an electrode disposed inside of the block such that a first surface of the electrode is exposed within the sample chamber and a second surface of the electrode is exposed within the Temperature control channel, the portion of the sample chamber being fluidically isolated from the temperature control channel by the electrode, the electrode being made of an electrically conductive material.

9. The apparatus of claim 8, wherein the first surface of the electrode defines at least a portion of a surface of the temperature control channel, the second surface of the electrode defines at least a portion of a surface of the sample chamber.

10. The apparatus of claim 8, wherein the block defines an electrode channel between the sample chamber and the temperature control channel, the entire electrode is disposed within the block and has a medial portion disposed within the electrode channel such that the temperature control channel is fluidically isolated from the sample chamber by the electrode.

11. The apparatus of claim 8, wherein the electrode and at least a first portion of the temperature control channel are aligned along a first axis, the temperature control channel has a second portion aligned along a second axis nonparallel to the first axis.

12. The apparatus of claim 8, wherein the electrode has a cylindrically shaped surface disposed between the first surface of the electrode and the second surface of the electrode, the electrode is disposed inside of the block such that the cylindrically shaped surface is fluidically isolated from the sample chamber.

13. The apparatus of claim 8, wherein the block is a monolithic block made of Teflon and the first surface of the electrode is made of stainless steel, the electrode has a cylindrically shaped surface between the first surface of the electrode and the second surface of the electrode.

14. The apparatus of claim 8, wherein the block defines a first opening of the temperature control channel on a first side of the block and defines a second opening of the temperature control channel on a second side of the block, the block defines an opening of the sample chamber on a third side of the block.

15. The apparatus of claim 8, wherein the sample chamber is configured to receive a sample through an opening of the sample chamber, the block defines an opening of a drain channel through which a sample included in the sample chamber is drained after a dielectric spectroscopy experiment has been completed, the opening of the sample chamber is on a side of the block opposite a side of the block including the opening of the drain channel.

16. A method, comprising:
   forming at least a portion of an electrode channel within a block, the block being made of an electrically insulating material;
   forming a sample chamber within the block such that the sample chamber is in fluid communication with the portion of the electrode channel; forming a temperature control channel within the block; and
   disposing an electrode inside of the electrode channel of the block such that a surface of the electrode is exposed within the sample chamber and a second surface of the electrode is exposed within the temperature control channel, the electrode being made of an electrically conductive material, the sample chamber being fluidically isolated from the temperature control channel by the electrode.

17. The method of claim 16, wherein
the temperature control channel is in fluid communication with the sample chamber via the portion of the electrode channel before the disposing and fluidically isolated from the sample chamber after the disposing.

18. The method of claim 16, further comprising:
forming a probe channel such that an ambient environment outside of the block is in fluid communication with the electrode channel.

19. The method of claim 16, wherein the electrode has a cylindrical shape, the first surface defining a curved portion of the cylindrical shape, the sample chamber has a diameter substantially equal to a diameter of the electrode.

* * * * *

UNITED STATES PATENT AND TRADEMARK OFFICE
CERTIFICATE OF CORRECTION

PATENT NO. : 8,593,164 B2  
APPLICATION NO. : 13/501864  
DATED : November 26, 2013  
INVENTOR(S) : Satyan Chandra et al.

Page 1 of 1

It is certified that error appears in the above-identified patent and that said Letters Patent is hereby corrected as shown below:

In the Claims

In column 20, line 9, in claim 8, delete "Temperature" and insert -- temperature --, therefor.

Signed and Sealed this
Twenty-first Day of July, 2015

Michelle K. Lee
*Director of the United States Patent and Trademark Office*